United States Patent [19]

Cidlowski et al.

[11] Patent Number: 4,465,776
[45] Date of Patent: Aug. 14, 1984

[54] MONOCLONAL ANTIBODIES TO VITAMIN $B_6$ AND IMMUNOASSAY METHOD

[75] Inventors: John A. Cidlowski, Chapel Hill, N.C.; Dace Viceps-Madore, Burlington, Vt.

[73] Assignee: Research Corporation, New York, N.Y.

[21] Appl. No.: 424,760

[22] Filed: Sep. 27, 1982

[51] Int. Cl.$^3$ ............................................... C07G 7/00
[52] U.S. Cl. ..................................... 436/504; 436/505; 436/527; 436/531; 436/548; 436/804; 436/808; 436/810; 436/815; 260/112 R; 260/112 B; 435/4; 435/7; 435/68; 435/172.1; 435/240; 435/810; 435/948; 435/172.2; 424/85; 424/88; 424/177; 935/89; 935/93
[58] Field of Search ........ 436/548, 505, 804, 808–810, 436/815, 527, 531, 504; 424/1, 1.1, 85, 88, 177; 435/172, 68, 417, 70, 240, 241, 948, 810; 260/112 R, 112.5 R

[56] References Cited

U.S. PATENT DOCUMENTS 3,981,863  9/1976  Niswender et al. .................. 536/25
4,172,124 10/1979  Koprowski et al. .................. 424/85
4,196,265  4/1980  Koprowski ............................ 435/2
4,209,614  6/1980  Bernstein et al. ..................... 536/25

OTHER PUBLICATIONS

Kohler, G. et al., Nature, vol. 256, pp. 495–497 (1975).
Kohler, G. et al., European Journal of Immunology, vol. 6, pp. 511–519 (1976).
Gefter, M. J. et al., Somatic Cell Genetics, vol. 3 (2), pp. 231–236 (1977).
Endres, D. B. et al., Clinical Chemistry, vol. 24 (3), pp. 460–465 (1978).
Houts, T. M. et al., Clinical Chemistry, vol. 27(2), pp. 263–267 (1981).
Jau, K. S. et al., Blood, vol. 26(2), pp. 202–214 (1965).
Schilling, R. I. et al., Clinical Chemistry, vol. 29(3), pp. 582–583 (1983).
Higgins, T. et al., Clinical Chemistry, vol. 29(3), pp. 587–588 (1983).
Kubasik, N. P. et al., Clinical Chemistry, vol. 26(5), pp. 598–600 (1980).
Kitter, Jason M., Dace Viceps–Madore, John A. Cidlowski, and J. W. Thanassi "Immunobolt Detection of Pyridoxal Phosphate Binding Proteins in Liver and Hepatoma Cytosolic Extracts", *Biochem. Biophys. Res. Comm.* 112(1):61(1983).
Kitter, Jason M., N. T. Meisler, D. Viceps–Madore, J. A. Cidlowski and J. W. Thanassi, "A General Immunochemical Method for Detecting Proteins on Blots", *Analytical Biochemistry* in press (1984).
Viceps–Madore, Dace, J. A. Cidlowski, J. M. Kittler and J. W. Thanassi, "Preparation, Characterization and Use of Monoclonal Antibodies to Vitamin $B_6$" J. Biological Chemistry 258:2689 (1983).

*Primary Examiner*—Benjamin R. Padgett
*Assistant Examiner*—M. Moskowitz
*Attorney, Agent, or Firm*—Scully, Scott, Murphy & Presser

[57] ABSTRACT

A continuous hybridoma cell line which secretes recoverable quantities of monoclonal antibodies having specificity against Vitamin $B_6$, which antibodies are useful in a method for detecting the presence of vitamin $B_6$ in an animal sample.

16 Claims, No Drawings

MONOCLONAL ANTIBODIES TO VITAMIN B6 AND IMMUNOASSAY METHOD

BACKGROUND OF THE INVENTION

The present invention arose out of work funded by the National Institutes of Health, Department of Health and Human Services, Grant No. AM 25316.

FIELD OF THE INVENTION

The present invention relates to immunoassay methods for the determination of vitamin B-6, which utilize monoclonal antibodies therefor.

BRIEF DESCRIPTION OF THE PRIOR ART

The biological activity of the vitamin $B_6$ group is displayed by pyridoxine, pyridoxal, pyridoxamine and their 5-phosphate esters. The biologically active coenzyme form is pyridoxal 5-phosphate, and the other compounds undergo enzymatic conversion in tissues to pyridoxal 5-phosphate. The vitamin is widely and uniformly distributed in all foods, muscle meats, liver, vegetables, and whole grain cereals among the best sources. (See Harrison's "Principles of Internal Medicine", Vol. 1, pages 427–428.)

Pyridoxal phosphate acts as a cofactor for an exceptionally large number of enzymes involved in amino acid metabolism, including transaminases, synthetases, and hydroxylases. It is of particular importance in humans in the metabolism of tryptophan, glycine, serine, glutamate, and the sulfur-containing amino acids. Pyridoxal phosphate is also required for the synthesis of the heme precursor δ-amino levulinic acid. A large share of body pyridoxine is found in muscle phosphorylase, where it may function not catalytically but to stabilize the enzyme. It also plays a vital role in neuronal excitability, possibly as a result of its function in transulfuration reactions or γ-amino butyric acid metabolism.

The widespread occurrence of the vitamin in food is probably the reason that a naturally occurring pure pyridoxine deficiency has never been recognized except when the pyridoxine content of food is destroyed during processing, as has occurred in some processed infant formulas. However, present pyridoxine deficiency is frequent in the United States. This happens because many commonly used drugs act as a pyridoxine antagonists. Such drugs include hydrazines such as isoniazid, cycloserine, an antituberculous drug, and penicillamine. Abnormal tryptophan metabolism and convulsions brought about by these antagonists can be prevented by supplementation with the vitamin.

There are also a large number of genetic conditions in which abnormalities in vitamin $B_6$ metabolism occur. One group, if not provided with daily supplements of pyridoxine during infancy, develops convulsions and brain damage and dies; these children have an apoenzyme for glutamic acid decarboxylase that has a decreased binding affinity for pyridoxal phosphate. Another group has pyridoxine responsive chronic anemia. (See also Mudd, S. H., "Pyridoxine-Responsive Genetic Disease" Fed. Proc. 30: 970 (1971)).

Estimates of vitamin deficiency have been based upon the cure of clinical signs of deficiency, the excretion of tryptophan metabolites after tryptophan-loading tests, measurement of various amino acid transferase activities in blood, and excretion of pyridoxine or its metabolites, or of oxalate in the urine. The most common index is the measurement of tryptophan metabolites, following tryptophan loading. Alternatively, cystathionine can be assayed after a methionine load. It is also possible to carry out measurement of red blood cell glutamic pyruvic transaminase in vitro, in the presence and absence of pyridoxal phosphate.

Other enzymic assays for pyridoxal phosphate include the pyridoxal dependence of enzymes such as tyrosine decarboxylase or tryptophanase, the activities of which vary directly with pyridoxal phosphate concentrations. Chabner B., and Livingston, D. (Analytical Biochemistry 34:413–423 (1970)) describe a method of measuring pyridoxal phosphate based on the measurement of $^{14}CO_2$ evolved during the decarboxylation of L-tyrosine-1-$C^{14}$ by pyridoxal phosphate dependent tyrosine apodecarboxylase from S. faecalis. This method includes a partially purified apoenzyme, a rapid assay procedure involving the apoenzyme and quantitative capture of evolved radioactive $CO_2$ in a removable potassium hydroxide-containing well which could be placed in scintillation fluid for immediate counting.

Given the importance of pyridoxal phosphate and related metabolites, and the necessity of accurately ascertaining levels thereof in animals, it would be useful if an alternative, rapid and efficient method for its assay could be provided.

A need therefore continues to exist for an assay of vitamin $B_6$ metabolites in animals.

SUMMARY OF THE INVENTION

It is therefore an object of the invention to provide a method for the determination of vitamin $B_6$ in animals.

It is another object of the invention to provide an immunoassay for the determination of vitamin $B_6$ and related metabolites.

Yet another object of the invention is to provide monoclonal antibodies against vitamin $B_6$ and related metabolites.

Still another object of the invention is to provide kits useful for the assay of vitamin $B_6$ and related metabolites in animals.

These and other objects of the invention as will hereinafter become more readily apparent have been attained by providing:

A method for detecting vitamin B-6 levels in an animal fluid wherein the improvement comprises using immunoassay techniques, with monoclonal antibodies to vitamin $B_6$.

Another object of the invention has been obtained by providing:

Monoclonal antibodies having specificity for antigenic preparations containing active forms of vitamin $B_6$.

BRIEF DESCRIPTION OF THE PREFERRED EMBODIMENTS

The present invention is based on the discovery that monoclonal antibodies against vitamin $B_6$ and related metabolites can be readily obtained if the immunization antigen comprises one or more proteins covalently bound to pyridoxal phosphate. The immunizing preparation can then be used to generate corresponding lymphocytes which, in standard hybridoma methodology, can be fused with an appropriate immortal cell line to give monoclonal antibody-yielding hybridomas.

The immunizing preparation comprises at least one protein which contains a free amino group or groups capable of reacting with the free aldehyde group of pyridoxal or its phosphate derivative. It may either be one protein attached to one or more pyridoxal moieties, or a multiplicity of proteins each (or at least some) of which are attached to one or more pyridoxal moieties.

Any protein which, when covalently bound to pyridoxal or pyridoxal phosphate is capable of yielding an immunogenically active preparation can be used. A classical example of a carrier protein is serum albumin or thyroglobulin.

In a preferred embodiment of the invention, which is particularly attractive because of the advantage of working with only partially purified proteins, a partially purified mixture of human cytoplasmic proteins is used. More preferably, the mixture is of 20-30 (as detectable by gel electrophoresis) DNA binding proteins from human placenta cells. This mixture can be isolated from human placentae essentially as described by Wrange et al (J. Biol. Chem. 254: 9284-9290 (1979)).

The covalent bond between one or more amine groups on the carrier protein or proteins and the pyridoxal or pyridoxal phosphate moiety ("hapten") is achieved by first incubating the hapten with the carrier protein for a time and under conditions sufficient to allow the formation of an imine bond between the aldehyde group on the hapten and one or more amino groups on the protein or proteins. Incubation under physiological buffer conditions, at temperatures between 0° and 37° C., for 5 minutes-2 hours are normally appropriate to form the imine bond or bonds.

Since the imine bonds are readily hydrolyzeable, it is necessary to fix the hapten moieties to the proteins with a more stable linkage, and this is achieved by reducing the imine (C=NH) bond to an amine (CH—NH) bond. Any reducing agent capable of transforming an imine to an amine bond under physiological conditions (e.g. aqueous solvent, neutral or close to neutral pH, temperatures between 0° C. and 37° C.), can be used. Among such reagents are hydride generating agents such as sodium borohydride (preferred), sodium cyanoborohydride, lithium aluminum hydride, and the like.

The preferred hapten is pyridoxal phosphate, although other vitamin $B_6$ derivatives or analogues can also be used, such as for example isosteric analogues thereof.

The preparation of hybridoma cell lines derived by fusing an immortal cell line and lymphocytes sensitized against the immunogenic preparation can be done by techniques which are well known to those who are skilled in the art. (See, for example, Douillard, J-Y. and Hoffman, T., "Basic Facts About Hybridomas," in: Compendium of Immunology Vol. II. L. Schwartz (Ed.) (1981); Kohler, G. and Milstein, C., Nature 256, 495-497 (1975); European Journal of Immunology, Volume 6 pp. 511-519 (1976), Koprowski et al, U.S. Pat. No. 4,172,124, Koprowski et al, U.S. Pat. No. 4,196,265, and Wands, U.S. Pat. No. 4,271,145, all of which are herein incorporated by reference.)

The choice of animal is dependent on the availability of appropriate plasmacytoma lines capable of fusing with lymphocytes thereof. Mouse and rat have been the animals of choice in hybridoma technology, and are preferably used. Humans can also be utilized as sources for sensitized lymphocytes if appropriate immortalized human (or nonhuman) cell lines can be fused therewith.

Injection into the animal can be carried out until the animal serum is positive to the immunogenic preparation. Usually the injecting material is emulsified in Freund's complete adjuvant. The detection of antibodies can be carried out by testing the antisera with appropriately labeled antigen. Lymphocytes can be obtained by removing the spleen of sensitized animals in a sterile fashion and carrying out fusion. Alternatively, lymphocytes can be stimulated or immunized in vitro.

A number of cell lines suitable for fusion have been developed and the choice of any particular line for hybridization protocols is directed by any one of a number of criteria such as speed, uniformity of growth characteristics, deficiency of its metabolism for a component of the growth medium, and potential for good fusion frequency. Intraspecies hybrids, particularly between like strains, work better than interspecies fusions. Several cell lines are available, including mutants selected for the loss of ability to secrete myeloma immunoglobulin. Included among these are the following mouse myeloma lines: $MPC_{11}$-X45-6TG, P3-NS1-1-Ag4-1, P3-X63-Ag8, or mutants thereof such as X63-Ag8.653, SP2-0-Ag14 (all BALB/C derived), Y3-Ag1.2.3 (rat), and U266 (human). The preferred line is X63-Ag8.653.

Cell fusion can be induced either by virus or polyethylene glycol. Although viruses have been progressively replaced by chemical agents as preferred fusion inducers, they may still be used, including HVJ, Epstein-Barr or Sendai virus. Polyethylene glycol (PEG) is the most efficacious agent for the fusion of mammalian somatic cells. PEG itself may be toxic for cells and various concentrations should be tested for effects on viability before attempting fusion. The molecular weight range of PEG may be varied from 1,000 to 6,000. In general it gives best results when diluted to 30-50% in saline or serum-free medium. Exposure to 30% PEG at 25° C. for 8 minutes seems best. Extremes of temperature should be avoided and preincubation of each component of the fusion system at 37° C. prior to fusion gives optimum results. The ratio between spleen cells and malignant cells should be optimized to avoid "cell fusion" among spleen cells. Myeloma/spleen cell ratios ranging from 1:1 to 1:10 give good results.

The successfully fused cells can be separated from the myeloma line by any technique available to the art. The most common and preferred method is to choose a malignant line which is Hypoxanthine Guanine Phosphoribosyl Transferase (HGPRT) deficient, which will not grow in an aminopterin-containing medium because of its inability to synthesize purines from thymidine and hypoxanthine. The selection medium used to allow only growth of hybrids is generally composed of hypoxanthine $1 \times 10^{-4}M$, aminopterine $1 \times 10^{-5}M$, and thymidine $3 \times 10^{-5}M$, commonly known as the HAT medium. The fusion mixture can be grown in the HAT-containing culture medium immediately after the fusion or 24 hours later. The feeding schedules usually entail maintainance in HAT medium for two weeks and then feeding with in either regular culture medium or hypoxanthine, thymidine containing medium.

The growing colonies are tested for the presence of antibodies that recognize the antigenic preparation as well as phosphopyridoxyl bovine serum albumin. Detection of hybridoma antibodies can be performed using assays where the antigen is bound to a solid support and allowed to react to hybridoma supernatants containing putative antibodies. The presence of antibodies may be detected by "sandwich" techniques using a variety of indicators. Most of the common methods are sufficiently sensitive for use in the range of antibody concentrations secreted during hybrid growth.

Cloning of hybrids can be carried out after 5–16 days of cell growth in selected medium. Cloning can be performed by limiting dilution in fluid phase or by directly selecting single cells growing in semi-solid agarose. For limiting dilution, cell suspensions are diluted serially to yield a statistical probability of having only one cell per well. For the agarose technique, hybrids are seeded in a semi-solid upper layer, over a lower layer containing feeder cells. The colonies from the upper layer may be picked up and eventually transferred to wells.

Antibody-secreting hybrids can be grown in various tissue culture flasks, yielding supernatants with variable concentrations of antibodies. In order to obtain higher concentrations, hybrids may be transferred into animals with inflammatory ascites. Antibody containing ascites can be harvested 8–12 days after intraperitoneal injection. The ascites contain a higher concentration of antibodies but include both monoclonal and immunoglobulins from the inflammatory ascites.

A number of monoclonal antibodies can be obtained by this method, each having different specificity. The specificities can vary from those that recognize only the phosphorylated forms of vitamin $B_6$, to those that recognize both phosphorylated and unphosphorylated forms. The obtained monoclonal antibodies are very discriminating between the different vitamers and specifically bind the active forms of vitamin $B_6$.

The detection of vitamin $B_6$ or any of its forms such as pyridoxal, pyridoxal phosphate, pyridoxamine, pyridoxine phosphate, pyridoxine, etc., is carried out by standard immunoassay methodology well known to those with skill in the art. An animal sample, such as a serum sample, feces sample, urine sample, or any other physiological fluid containing or suspected of containing vitamin $B_6$ is tested by such known immunoassay methodology.

For example, in competitive immunoassay, a sample containing $B_6$ is incubated with an anti $B_6$ monoclonal antibody and a detectably labeled $B_6$ molecule. Among the detectable labels usable in the present invention are radiolabels, enzyme labels, chromophoric labels or other labels.

Radiolabels for example can be divided into two types: those with an internal label and those with an external label. With an internal label an existing atom in the the $B_6$ moiety is replaced by a radioactive isotope of that atom (e.g., $^{14}C$ for $^{12}C$, $^{32}P$ for $^{31}P$, etc.). Only the internal label methodology can be used in the present invention.

Labels other than radioactive labels might be used since they are well known in generalized binding assay techniques, with the critical limitation, of course, that they do not alter the immunogenicity of $B_6$. Thus, for example, alternatives to isotopic labels may be (a) chromophoric labels such as fluorescent, ultraviolet absorbing or visible light absorbing labels. These are advantageous because of their long shelf life in the absence of radiation. (b) Enzyme labels: since specific enzymes can be coupled to other molecules by covalent links, a highly specific enzyme may be covalently reacted. (See, e.g., Schuurs, A. H. W. M. and Van Weemen, B. K. Clinica Chim. Acta 81: 1–40 (1977) or Schuurs, U.S. Pat. No. Re 29,169, herein incorporated by reference.) (c) Other tracers: free radical labels or bacterial labels can also be used in the present invention.

The general competitive binding assay techniques useful for detection of minute amounts of organic molecules are well known in the art. Any of these competitive binding assay techniques can be used for the purposes of the present invention. If $B_6$ is present in the sample, it will compete with detectably labeled $B_6$ for the monoclonal antibody binding sites. The more unknown $B_6$ is present, the less the labeled $B_6$ will be bound by the antibody.

It is then necessary to determine the distribution of labeled $B_6$ between the free and the bound form. Usually but not always, this requires that the bound fraction be physically separated from the free fraction; a variety of techniques can be used for that purpose. All of these techniques exploit physical-chemical differences between the labeled $B_6$ and its free and bound form. These techniques include adsorption of free antigen to solid phase material, such a cellulose, charcoal, silicates or ion exchange resins; precipitation of antigen/antibody complexes by second antibody or Protein A; salting out techniques or organic solvents; adsorption or complexing of antibody to solid phase material; electrophoretic separation on cellulose, starch gel or polyacrylamide gel, and the like.

The choice of technique depends on the speed, simplicity, applicability and cost. It is a simple matter of choice for anyone skilled in the art and therefore, the generalized techniques will not be described in further detail.

Particularly preferred among the aforementioned techniques are the solid phase systems. When the monoclonal antibody is covalently coupled to a insoluble support, both it and the bound complex can readily be separated from the soluble free fraction. A wide variety of solid phase supports have been described which include particles of dextran and cellulose, and continuous surfaces such as polystyrene and polypropylene discs, or the walls of plastic or glass tubes or slides. Plastic surfaces exhibit adsorptive properties, and simply exposing such surface to an appropriate dilution of the monoclonal antibody will lead to the attachment of a proportion of the antibody molecules thereon. The bond is probably ionic or hydrophobic, and not covalent. Covalent bonding, however, can be readily obtained by the incorporation of cross-linking agents such as glutaraldehyde and other agents in the antibody solution used for the coating.

Coated tube systems offer great convenience in the actual performance of assays and the technique can be widely used in commercial kits.

In one preferred embodiment, the antibody is covalently attached to the inside of a test tube and labeled $B_6$ is incorporated in the tube. A single addition of a sample fluid being tested is then added to the test tube. After incubation, the contents of the tube are emptied and the tracer is detected by standard methodology.

Another preferred embodiment is the use of a "sandwich" immunoassay (simultaneous, forward or reverse modes) wherein solid phase bound monoclonal anti-$B_6$ is incubated with the animal sample containing $B_6$, followed (or simultaneously) by incubation with a second anti-$B_6$ antibody (which may or may not be monoclonal). The second antibody is normally detectably labeled, as for example with an enzyme. Sandwiching of $B_6$ occurs only if $B_6$ is present in the sample being tested, and detection of the label is therefore an indication of the presence of $B_6$ in the sample.

The monoclonal antibody can be attached to a particulate solid phase by any one of a number of techniques designed to yield a covalent link between the protein and the particles, such as for example diazotization or cyanogen bromide. The resulting material is extensively washed to insure that no free monoclonal antibody molecules remain. Alternative approaches include the use of antibody entrapped in the interstices of a polyacrylamide gel or covalently bound to magnetic particles. With the latter system, mixing and separation can be simply achieved by the application of magnetic field.

Detection of the label by some physical or chemical means is usually necessary. When the label is an enzyme, the enzyme is assayed by the addition of a substrate which upon reaction releases an ultraviolet or visible light absorbing product. For example, the enzyme may be alkaline phosphatase assayed by the hydrolysis of p-nitrophenylphosphate, which releases p-nitrophenol having a large absorption coefficient at 400 nm. Appearance of yellow coloration is a direct indication of the presence of $B_6$ in the animal sample.

Still another immunoassay method included in the present invention is the so-called "latex particle aglutination technique." This technique does not involve the use of a detectably labeled $B_6$ or enzyme linked technology. See for example Sawai et al, U.S. Pat. No. 4,118,192 or Hoffmann, British Pat. No. 1,384,399. In these techniques monoclonal antibody raised against $B_6$ is supported on an insoluble carrier particle, usually a latex particle, thus sensitizing the insoluble particle. The supported monoclonal antibody is then reacted with a sample suspected of containing $B_6$. The sensitized latex agglutinates to a degree which is proportional to the amount of $B_6$ present in the sample. The agglutination is followed by irradiating the resulting reaction mixture with light having a wavelength in the range of 0.6–2.4 microns. The determination of absorbance can be performed with a spectrophotometer similar to that used in near infrared spectrometry. Polystyrene latexes or styrene-butadiene latexes can readily be used; however, other particles such as dispersed coccal bacteria, cell membrane fragments, micro particles of inorganic oxides such as silica, silica alumina, and alumina or pulverized minerals, metals and the llike are also readily usable. The latex agglutination techniques not only make it possible to determine low concentrations of $B_6$ but enable the determination of the $B_6$ in trace amounts and with comparable specificity to those of the radio or enzyme immunoassay methodology. The amount of $B_6$ can be determined by measuring the absorbance as described above or, alternatively, by measuring the rate of reaction, or the reaction time required for the absorbance to reach a prescribed value.

The Sawai et al methodology is also applicable in the inhibition of agglutination mode. In this mode, latex particles are coated with phosphopyridoxyl-protein. The particles are then incubated with monoclonal antibody. The formed complex is mixed with samples suspected of containing $B_6$. If a sample contains $B_6$, the latter will compete for the antibody binding site and inhibit the agglutination of the protein-$B_6$-covered latex particles.

The techniques and materials of the present invention for the detection of $B_6$ and related metabolites or derivatives can be readily automated. A noteworthy development in the field of automated radioimmunoassay is the recent patent of Brooker et al, U.S. Pat. No. 4,022,577.

Among the kits useful in the present invention are those of the general type described by Szczesniak, U.S. Pat. No. 3,899,298. Such kits comprise a carrier being compartmentalized to receive at least one, or at least two or at least three or more containers and to maintain said containers in closed confinement. A first container may contain purified anti-$B_6$ monoclonal antibody, either in solution, in freeze-dried form or covalently bound to the inside thereof, such as for example if such container is a test tube. A second container may then contain a second monoclonal anti-$B_6$ antibody or a non-monoclonal antibody. Alternatively, another container may contain detectably labeled $B_6$. At the time of testing for $B_6$ in the sample, the sample is added to the first container containing the monoclonal antibody, incubated, and then antibody from the second container is added thereto to provide a "sandwich". The antibody in the second container may be detectably labeled as, for example, by a radio label or an enzyme label. Another container in the kit may contain appropriate enzyme substrate in order to carry out the "ELISA" methodology. Any number of variations or permutations consistent with the various techniques for use in the detection of $B_6$ can be envisioned for the preparation of a kit. These are all matters of choice, determined by the ease of handling, rapidity and efficiency of the testing.

Quantitative analysis of $B_6$ can be carried out by interpolation into a standard curve, as is known in the art. A multiplicity of container means, each one having a different amount of $B_6$, can be present in the kit for such a purpose.

In still another embodiment, the monoclonal antibody can be immobilized onto plastic strips which are then brought into contact with the samples suspected of containing $B_6$ or a derivative thereof. Subsequently, the strip is contacted with a solution containing a second, enzyme labeled anti-$B_6$, or a derivative thereof; this results in a sandwich forming on the strip. Finally, introduction of the strip into a color developing solution (such as substrate for the enzyme) and detection of color, is a rapid, efficient and inexpensive method for qualitatively, and even roughly quantitatively determining $B_6$ in animal samples.

The presence of $B_6$ can be detected in any of the previously mentioned disease states, as well as during pregnancy. The immunoassay of the present invention uses antibodies which are very discriminating between the different vitamers and especially bind the active forms of vitamin $B_6$. The methodology described herein is far superior in sensitivity and ease to presently used enzyme assays for pyridoxal and derivatives thereof.

One of the most useful applications of anti $B_6$ antibodies is in the detection and isolation of cellular pyridoxal phosphate-binding proteins. Virtually nothing is known at present about the roles of pyridoxal phosphate-dependent enzymes and other pyridoxal phosphate-binding cellular components in growth, development, differentiation and carcinogenesis. The only experiments along these lines have been reported by Bosron et al (J. Biol. Chem. 253: 1488–1492 (1978)) who studied pyridoxal phosphate-binding proteins in normal rat liver cytosols. These investigators employed molecular sieve and ion-exchange chromatography, methods which are severely limited in their selectivity. Immunoblot detection iof pyridoxal phosphate-binding proteins in rat liver cytosol is highly sensitive and displays great resolving power. The fact that Pansorbin can precipitate the antiphosphopyridoxal monoclonal antibodies provides a means to use the antibodies to selectively isolate pyridoxal phosphate-binding proteins from complex mixtures.

Another use of these antibodies lies in the field of steroid hormones where pyridoxal phosphate has proven to be a valuable tool in the study of the properties of steroid hormone receptors. Preliminaty data, for example, indicates that these antibodies will interact with pyridoxal phosphate-treated borohydride reduced thymocyte glucocorticoid receptors. This provides the first direct evidence that exposure of a hormone receptor to pyridoxal phosphate results in derivatization of the receptor. This observation suggests that the monoclonal anti-phosphopyridoxyl antibodies can be useful in the physical characterization of glucocorticoid and other steroid receptors.

Having now generally described this invention, the same will be better understood by reference to certain specific examples which are included herein for purposes of illustration only and are not intended to be limiting unless otherwise specified.

EXAMPLE

Materials and Methods

Materials. Female BALB/c mice for immunization were obtained from Timco Breeding Labs, Houston, Tex. Sprague-Dawley rats were from Canadian Breeding Farms, Wilmington, Mass. Dulbecco's modified Eagle's medium with 4.5 g glucose/L, calf serum, nonessential amino acids and penicillin/streptomycin were from GIBCO Laboratories, Grand Island, N.Y. Methionine-free Eagle's minimum essential medium was purchased from Flow Laboratories, McLean, Va. Goat antimouse $Fab_2$ antisera conjugated with horse-radish peroxidase was from Northeast Biomedical Laboratory, Inc., South Windham, Maine. Cell culture plates (24 and 96 wells) and polyvinyl chloride plates (96 wells) were from Costar, Cambridge, Mass. and Dynatech Laboratories, Inc., Alexandria, Va., respectively. Polyethylene glycol 1000 was purchased from Baker Chemical Co., Phillipsburg, N.J. Hypoxanthine, aminopterin, thymidine, phosphorylase b, bovine serum albumin (fraction V;BSA) Tween-20, o-phenylenediamine, 3,3'-diaminobenzidine and pyridoxal, pyridoxamine and pyridoxamine-5'-phosphate hydrochlorides were from Sigma Chemical Co., St. Louis, Mo. Pyridoxal-5'-phosphate and pyridoxine hydrochloride were from Aldrich Chemical Company, Milwaukee, Wis. Pyridoxine-5'-phosphate was prepared by reduction of pyridoxal-5'-phosphate with sodium borohydride. Phosphopyridoxyl bovine serum albumin was prepared according to the procedure of Cordoba et al (Biochem. Biophys. Acta 127: 151–158 (1966)). Borohydride-reduced phosphorylase b, containing one phosphopyridoxyl residue per molecule was prepared by the procedure of Strausbauch et al (Methods in Enzymology XI, 671–675). L-[$^{35}$S]Methionine was from New England Nuclear, Boston, Mass. Nitrocellulose paper (pore size, 0.15$\mu$) was a product of Schleicher and Schuell, Inc., Keene, N.H. Calbiochem-Behring Corporation, La Jolla, Calif., was the supplier of Sansorbin and Pansorbin. Human sera was obtained from healthy adults. Vitamin B-6 depleted sera was prepared as described by Lipson et al (Arch. Biochem. Biophys. 204: 486–493). Vitamin B-6 supplemented sera was obtained by addition of exogenous pyridoxal phosphate to sera to a final concentration of 0.1 mM. Sera were diluted 1:2 with 0.9% NaCl prior to addition of pyridoxal phosphate, and subsequently reduced with $NaBH_4$, as described below for antigen preparation. All sera were dialyzed against phosphate-buffered saline, unless designated as fresh sera. All other chemicals were reagent grade or the highest quality available.

Antigen Preparation. Pyridoxal phosphate was reductively and covalently linked to a mixture of DNA binding proteins having a high affinity for glycocorticoids. This mixture of proteins was isolated from human placentae essentially as described by Wrange et al (J. Biol Chem. 254: 9284–9290 (1979)). The last step in the purification of this class of proteins involves their elution from a DNA cellulose column with 10 mM pyridoxalphosphate. To this eluate was added solid sodium borohydride, with ice-cooling, until the yellow color was bleached. This procedure yields a mixture of proteins derivatives at lysine residues with the phosphopyridoxyl group which immunologically acts as a hapten. The phosphopyridoxyl-proteins obtained in this fashion were freed from low molecular weight products and reagents by dialysis. SDS-polyacrylamide gel electrophoresis (SDS-PAGE) indicated the presence of at least 10 Coomassie blue-staining proteins having molecular weights in the range of 25K to 100K daltons.

Immunization and Fusion: Female BALB/c mice (El-4,E6) were injected intraperitoneally with 115 $\mu$g of phosphopyridoxyl-reduced proteins in Freund's complete adjuvant. A second intraperitoneal injection (115 $\mu$g) was given 7 weeks (E1-4) or 8 weeks (E6) later in incomplete adjuvant. Two months later, each mouse received an intravenous injection with 230 $\mu$g of antigen. On the third day post intravenous injection, mice were sacrificed and the spleens were removed aseptically. Fusion of spleen cells and myeloma cells (X63-Ag8.653) was carried out essentially as described by Gefter et al (Somat. Cell Genetics 3: 231–236 (1977)). Spleen cells were mixed with murine myeloma cells at a ratio of 4:1 and exposed to 35% polyethylene glycol 1000 for 8 min at 25° C. The cells were then resuspended in Dulbecco's modified Eagle medium supplemented with 100 $\mu$M hypoxanthine, 10 $\mu$M aminopterin, 30 $\mu$M thymidine, 20% calf serum, 0.1 mM nonessential amino acids, 10% NCTC 109, 100 units penicillin/mL, 100 $\mu$g streptomycin/mL, and dispensed (2.5×10$^4$ myeloma cells/well) in 96 well tissue culture plates. The cultures were incubated at 37° C. in a humidified 10% $CO_2$ incubator. Visible colonies appeared within one to two weeks. The supernatants were removed from these colonies and tested for desired monoclonal antibody production by an enzyme-linked immunosorbent assay (ELISA) described below. Desired colonies were recloned by limiting dilution on Sprague-Dawley thymus feeder layers (10$^7$ cells/well of 96 well plates). After initial selection of desired clones, it was necessary to supplement the growth medium with 4 mM pyridoxal and 0.5 mM pyridoxamine phosphate, presumable to counteract a hybridoma-caused vitamin B-6 deficiency.

ELISA. The antigen preparation or phosphopyridoxyl-BSA at a concentration of 10 ng/100 $\mu$l in 50 mM carbonate/bicarbonate (coating) buffer (pH 9.6) was applied into the wells of 96-well polyvinyl chloride microtiter plates; maximum binding of phosphopyridoxyl-BSA occurred at an applied concentration of 50 ng/well. After 2 hours at 25° C., the wells were filled with 1% BSA in coating buffer and kept overnight at 4° C. Unbound protein was washed off with 10 mM phosphate-buffered saline (pH 7.4) containing 0.05% Tween 20 (PBS-T) (3 washes, 2 minutes each). Antibody-containing hybridoma test supernatants were diluted 1:10 into 1% BSA in PBS-T (PBS-BSA-T); 100 μL aliquots were added to the antigen-coated wells. Following an overnight incubation at 4° C., unbound antibody was removed and the wells were washed 3 times with PBS-T (2 minutes each time). To the wells were then added goat anti-mouse Fab$_2$-horseradish peroxidase conjugate (100 μL) that had previously been diluted 1:10,000 with PBS-BSA-T. After 45 minutes at 37° C., unbound second antibody was removed and the wells were washed with PBS-T as described above. Substrate for horseradish peroxidase was added to each well (150 μL of a 0.006% solution of H$_2$O$_2$ in 0.1 M sodium citrate buffer, pH 5.0, containing 1 mg o-phenylenediamine/mL). The enzymatic reaction was stopped after 1 hr at 25° C. by the addition of 75 μL of 4M sulfuric acid. Absorbancies in the wells were measured at 490 nm on a Dynatech microtiter plate ELISA reader.

Saturation Analysis by ELISA. Monoclonal antibody-containing supernatants (10 μl) from hybridomas were mixed with 100 μl of $10^{-2}$ to $10^{-10}$M solutions of the six vitamer forms of vitamin B-6 in PBS-BSA-T or in human sera as indicated. After incubation at 4° C. for 24 hr, the vitamer/antibody mixtures were transferred into 96-well microtiter plates that had been previously coated with 10 ng phosphopyridoxyl-BSA/well as described above. After 24 hours at 4° C., unbound proteins were removed with three two-minute washes with PBS-T. The second antibody was added as described above and the plates incubated at 37° C. for 30 minutes and at 25° C. for 2-4 hr. The rest of the ELISA was carried out as described previously.

Immunoblot Detection of Pyridoxal Phosphate-Binding Proteins With Monoclonal Anti-Phosphopyridoxyl Antibodies. Rat liver cytosolic preparations were obtained as described previously except that liver was homogenized with 3 volumes of 0.25M sucrose instead of 9 volumes. SDS-PAGE was performed on a Hoefer SE600 apparatus using a 7.5% running gel and a 5% stacking gel. Gels were 1.5 mm thick and contained 150 μg of protein/well.

Cytosolic extracts (0.5 ml) were all treated with 0.15 ml of a 3% aqueous sodium borohydride solution for 30 minutes at 4° C. in order to reductively and covalently link endogenous and/or added pyridoxal phosphate to proteins as phosphopyridoxyl residues; the total volume of the reduction mixture was 3.0 ml (with PBS). All borohydride reduced samples were dialyzed for 24 hrs against PBS prior to application to gels. The pyridoxal phosphate content of liver cytosols was decreased by an initial dialysis against 5 mM hydroxylamine in 10 mM PBS at pH 7.4, followed by dialysis against PBS alone, prior to treatment with borohydride. Alternatively, the pyridoxal phosphate content of cytosols was increased by incubation (37° C., 30 min) with pyridoxal phosphate at a final concentration of 0.1 mM prior to treatment with borohydride. After the SDS-PAGE, proteins were horizontally electroeluted onto nitrocellulose paper using a Bio-Rad Trans-Blot ® cell. Transfer of proteins from the gel to the nitrocellulose paper was confirmed by staining the nitrocellulose blots with amido black.

Immunoblot detection of cystosolic proteins containing the phosphopyridoxyl group was carried out with monoclonal anti-phosphopyridoxyl antibody-containing ascites fluid obtained from mice inoculated intraperitoneally with hybridomas of interest. The ascites fluid obtained from mice innoculated with a hybridoma designated E6(2)2 was diluted with 1:500,000 with 1% BSA in PBS for use in the immunoblot procedure. The nitrocellulose papers containing borohydride-reduced liver cytosolic proteins were initially incubated for 30 minutes at 37° C. with 1% BSA in 10 mM PBS which was also 2.5% in human plasma. The human plasma was obtained from a local blood bank and had been previously dialyzed against 5 mM hydroxylamine in PBS as described above in order to remove endogenous pyridoxal phosphate. We have determined that this procedure removes 90-95% of the pyridoxal phosphate from human plasma as measured by an assay which involves the activation of pyridoxal phosphate-dependent tyrosine apodecarboxylase. After the BSA/human plasma/PBS coating solution was decanted, the nitrocellulose paper was incubated with gentle shaking in 0.3% H$_2$O$_2$ in PBS for 30 min followed by three 10 min washes with PBS. Diluted monoclonal antibody-containing ascites fluid was added to the nitrocellulose blot. After incubation for 90 min at 37° C. and then overnight at 4° C. with gentle shaking, the nitrocellulose paper was washed three times with PBS-T (10 min/wash). Second antibody (horseradish peroxidase-contjugated goat antimouse Fab$_2$ diluted 1:10,000 in 1% BSA in PBS) was added and the mixture was gently shaken for 90 min at 37° C. followed by 2½ hr at 4° C. The second antibody solution was decanted and the nitrocellulose paper was washed 3 times with PBS-T (ten minutes/wash). Staining solution was then added. Its composition was 30 mg diaminobenzidine in 100 ml of 50 mM Tris-HCl buffer (pH 7.6) containing 17 μL of 30% hydrogen peroxide; this solution was gassed in nitrogen and filtered before use. Incubation with staining solution was carried out at room temperature and was allowed to proceed until the desired intensity of color was obtained. This usually occurs within 5-10 minutes. Staining solution was then removed by washing with water. The developed immunoblot is stored in water until it could be photographed or dried for permanent storage.

Results

Development of Monoclonal Antibodies. Fusion of spleen cells obtained from mice immunized with a mixture of phosphopyridoxyl-proteins with murine myeloma cells, X63-Ag8.653, yielded 87 rapidly growing hybridomas (Table 1).

TABLE I

Hybridoma Yields Following Fusion of Myeloma Cells with Spleen Cells from Immunized Mice

| Mouse | Number of Clones | | |
|---|---|---|---|
| | Total | Ag$^+$ | PPxy-BSA |
| E1 | 14 | 5 | 4 |
| E2 | 20 | 6 | 4 |
| E3 | 2 | 0 | N.D. |
| E4 | 39 | 12 | 8 |
| E6 | 12 | N.D. | 2 |

Mice were immunized with phosphopyridoxyl-proteins, and myeloma-spleen cell fusions were carried out as described in Materials and Methods. Supernatants from hybridomas were tested by ELISA for monoclonal antibody specificity towards the antigen preparation (Ag$^+$) and to phosphopyridoxyl-bovine serum albumin (PPxy-BSA). N.D. represents not determined.

Screening of the supernatants of the clones by ELISA revealed that approximately 30% of them produced antibodies that bound to the antigen preparation used in the immunization regimen. To further investigate their antigenic specificity, the monoclonal antibodies were tested against phosphopyridoxyl-BSA by ELISA in order to determine their reactivity towards the hapteni phosphopyridoxyl group. Most of the monoclonal antibodies bound to phosphopyridoxyl-BSA (Table 1) but not to BSA, indicating that the phosphopyridoxyl group was a common haptenic antigen. In fact, eighteen hybridoma cell lines fell into this category.

Hybridoma cell lines were grown in media containing [$^{35}$S]methionine, and the immunoglobulins analyzed by SDS-PAGE. The autoradiograph showed that the monoclonal antibodies belong to the IgG class. The hybridoma-produced immunoglobulins could be precipitated with Protein A. *Staphylococcus aureus* cells without Protein A (Sansorbin) did not precipitate $^{35}$S-methionine labeled immunoglobulins from hybridoma supernatants. In contrast, Protein A-containing *Staphylococcus aureus* cells (Pansorbin) precipitated these immunoglobulins.

Relative Affinities of Monoclonal Antibodies for Phosphopyridoxyl-BSA. The affinity of each antibody for phosphopyridoxyl-BSA was determined by competition saturation analysis. Monoclonal antibodies were incubated with varying concentrations of phosphopyridoxyl-BSA prior to adding them to microtiter plates whose wells had been previously coated with the same antigen. By this quantitative blocking assay, the relative affinities of the monoclonal antibodies for phosphopyridoxyl-BSA in solution can be determined. The data indicated that some antibodies (E4(4)1, E2(1)9, E4(3)3) bind to phosphopyridoxyl-BSA more avidly than others (E4(3)5, E6(2)2 or E2(1)2).

Relative Affinity of Monoclonal Antibodies for B-6 Vitamers. Similar competitive saturation analyses were performed to determine the relative affinities of the monoclonal antibodies for the various B-6 vitamer forms. The monoclonal antibodies were incubated with $10^{-2}$ to $10^{-10}$M solutions of pyridoxal, pyridoxamine, pyridoxine and their 5'-phosphates (24 hr, 4° C.) prior to being added to the wells of microtiter ELISA plates that had been coated with phosphopyridoxyl-BSA. Antibody bound to the phosphopyridoxyl-BSA in the microtiter plate wells as then measured as described in Materials and Methods, i.e. by addition of horseradish peroxidase conjugated second antibody followed by addition of substrate. Each monoclonal antibody displayed a characteristic selectivity. Some common properties of the monoclonal antibodies are the following. They preferentially bind to the phosphorylated B-6 vitamers. The phosphate group by itself is not a major determinant of antigen-antibody interaction as the reactions are carried out in phosphate buffers. Some of the monoclonal antibodies can recognize the nonphosphorylated B-6 vitamers, (e.g. E1(4)1, E1(2)1, E2(2)1, E4(4)11, and E6(4)1). When the relative affinities for the B-6 vitamer forms are compared, all of the monoclonal antibodies except for a few (E1(2)1, E1(4)1 and E4(3)3) preferentially bind pyridoxamine phosphate. These exceptions appear to bind equally well to pyridoxine phosphate and pyridoxamine phosphate. Most of the monoclonal antibodies detect pyridoxine phosphate at lower concentrations than pyridoxal phosphate. Others, (e.g. E2(1)9, E2(2)1, E2(1)2, E4(3)5 and Eg(2)2) have similar affinities for pyridoxine phosphate and pyridoxal phosphate. These variations in specificity reflect differences in the antigenic sites. Since the haptenic antigens differ only in the presence or absence of the 5'-phosphate group and in the substitution at C4', it is apparent that the antibodies can discriminate among small structural differences in the antigens. In addition, it is likely that association of some of the vitamers with BSA, present in the incubation buffers, has an effect on antigenic behavior. This would be particularly so in the case of pyridoxal phosphate.

Detection of Vitamin B-6 in Human Serum. Blocking assays such as those described above are useful in measuring vitamin B-6 in biological material, such as serum samples. To test the sensitivity of this assay, various dilutions of human serum samples were incubated with antibody preparations obtained from two hybridomas (E6(2)2 or E6(4)1). Unbound antibodies were then quantitated by ELISA. The data indicated that the monoclonal antibodies are capable of detecting B-6 vitamers in serum proportional to their concentration. To confirm the validity of the data similar assays were performed with pyridoxal phosphate-depleted serum samples and pyridoxal phosphate-supplemented serum samples. The results indicated that when the pyridoxal phosphate content of serum is depleted by dialysis against buffered hydroxylamine, the blocking assay yielded values similar to those obtained when the sera were diluted with buffer. Conversely, addition of pyridoxal phosphate to serum followed by reduction with borohydride resulted in more antibody binding by the pyridoxal phosphate-supplemented serum relative to control serum samples. Finally, saturation analysis curves were identical when known concentrations of B-6 vitamers were prepared in either human sera or PBS. Thus, these data taken together suggest that monoclonal antiphosphopyridoxyl antibodies are of great use in the assessment of vitamin B-6 levels in serum samples.

Discussion

Immune serum containing (polyclonal) antibodies to the haptenic phosphopyridoxyl group has been prepared by immunization of rabbits with phosphopyridoxyl-BSA (Cordoba et al, Bioch. Bioph. Acta 127: 151-158 (1966)). In addition, antibodies to the pyridoxyl group have been raised in rabbits by immunization of the animals with pyridoxyl-poly-D,L-alanine-polylysine (Jaton, J. C. et al. Methods in Enzymology XVIII, A, 609-611 (1970)).

The introduction of monoclonal antibody techniques in this invention has led to develop monoclonal antibodies to the phosphopyridoxyl group to test whether such antibodies might be valuable tools in the study of vitamin B-6 in its various roles.

The monoclonal antibodies obtained are IgG immunoglobins against the phosphopyridoxyl group. Each line has it own unique characteristic vitamer-binding properties when tested against the different B-6 vitamer forms. The general preference displayed by the antiphosphopyridoxyl monoclonal antibodies for pyridoxamine phosphate probably reflects the fact that the protein linkage to the haptenic phosphopyridoxyl group is an ε-amino group of a lysine residue, and hence the phosphopyridoxyl group is an amine derivative most resembling pyridoxamine phosphate.

The data indicate the usefulness of the antiphosphopyridoxyl monoclonal antibodies in immunoassay methods for the determination of vitamin B-6 nutritional status. Pyridoxal phosphate, pyridoxal and pyridoxine are reported to be the predominant forms of vitamin B-6 in human blood plasma with very little pyridoxamine or pyridoxamine phosphate and no measurable pyridoxine phosphate. With the battery of monoclonal antibodies now available, one can develop methods to determine the phosphorylated and non-phosphorylated B-6 vitamer composition of plasma samples. For example, a serum sample can be treated with sodium borohydride to quantitatively convert serum pyridoxal phosphate, which is known to be bound to albumin, to phosphopyridoxyl-albumin. A monoclonal antibody (such as E4(3)5) which is highly selective for phosphorylated B-6 vitamer forms can be used in an ELISA to quantitate pyridoxal phosphatederived phosphopyridoxyl-albumin. A subsequent ELISA assay, using another monoclonal antibody, (such as E1(4)1) that binds well to unphosphorylated vitamer forms can then be used to quantitate the amounts of such vitamers. Thus monoclonal anti-phosphopyridoxyl antibodies provide the basis for clinical immunoanalyses of B-6 vitamers. Such analyses are not now routinely performed because the currently available methods involve relatively complicated techniques requiring high performance liquid chromatography, ion-exchange chromatography, microbiological or enzymatic assay methods.

Note: Cell line E6(2)2 has been deposited at the ATCC, having access No. HB 8172. It produces monoclonal antibodies of the IgG type against $B_6$ vitamers, most specifically against pyridoxine phosphate.

Having now fully described this invention, it will be understood by those of ordinary skill in the art that the same can be performed within a wide and equivalent range of parameters, conditions and methodology without affecting the spirit or scope of the invention or any embodiments thereof.

What is claimed as new and intended to be covered by Letters Patent of the United States is:

1. A murine monoclonal antibody of the IgG class which is specific for vitamin $B_6$.
2. The antibody of claim 1 wherein said vitamin $B_6$ is selected from the group consisting of pyridoxal, pyridoxine, pyridoxamine and phosphate esters thereof.
3. The antibody of claim 1 wherein said vitamin $B_6$ is the biologically active form.
4. The antibody of claim 1 in detectably labeled form.
5. The antibody of claim 4 wherein said label is an enzyme label, a chromophore label or a radiolabel.
6. The antibody of claim 1 which is immobilized on a solid phase.
7. The antibody of claim 6 wherein said solid phase is plastic, glass or latex.
8. The antibody of claim 6 wherein said solid phase is a slide, a tube or a plastic strip.
9. A kit useful for the detection of vitamin $B_6$ in a sample which comprises:
   a carrier being compartmentalized to receive one or more container means in close confinement therein,
   a first container means comprising a murine monoclonal antibody of the IgG class which is specific for vitamin $B_6$;
   a second container means comprising a detectably labeled antibody which is specific for vitamin $B_6$.
10. A kit useful for the detection of vitamin $B_6$ in a sample which comprises:
    a carrier being compartmentalized to receive one or more container means in close confinement therein,
    a first container means comprising a murine monoclonal antibody of the IgG class which is specific for vitamin $B_6$;
    a second container means comprising detectably labeled vitamin $B_6$.
11. The kit of any of claims 9 or 10 wherein said monoclonal antibody in said first container means is immobilized on said container means.
12. The kit of claim 9 wherein said antibody in said second container is labeled with a radiolabel, an enzyme label or a chromophore.
13. The kit of claim 9 wherein said antibody in said second container means is a monoclonal antibody.
14. The kit of any of claims 9 or 10 which also comprises a multiplicity of container means with different amounts of vitamin $B_6$.
15. The kit of any of claims 9 or 10 wherein said vitamin $B_6$ is the biologically form thereof.
16. The kit of any of claims 9 or 10 wherein said container means is a tube.

* * * * *